US009814909B2

United States Patent
Levy et al.

(10) Patent No.: US 9,814,909 B2
(45) Date of Patent: Nov. 14, 2017

(54) REFERENCE-BASED MOTION TRACKING DURING NON-INVASIVE THERAPY

(71) Applicants: INSIGHTEC, LTD., Tirat Carmel (IL); Yoav Levy, Hinanit (IL); Yoav Medan, Haifa (IL); Kobi Vortman, Haifa (IL)

(72) Inventors: Yoav Levy, Hinanit (IL); Yoav Medan, Haifa (IL); Kobi Vortman, Haifa (IL)

(73) Assignee: INSIGHTEC, LTD., Tirat Carmel ( * ) Notice: Subject to any disclaimer, the term of this patent is extended or adjusted under 35 U.S.C. 154(b) by 72 days.

(21) Appl. No.: 14/377,062

(22) PCT Filed: Feb. 6, 2013

(86) PCT No.: PCT/IB2013/000321
§ 371 (c)(1),
(2) Date: Aug. 6, 2014

(87) PCT Pub. No.: WO2013/117991
PCT Pub. Date: Aug. 15, 2013

(65) Prior Publication Data
US 2015/0016682 A1    Jan. 15, 2015

Related U.S. Application Data

(60) Provisional application No. 61/595,338, filed on Feb. 6, 2012, provisional application No. 61/595,341, filed on Feb. 6, 2012.

(51) Int. Cl.
*G06K 9/00* (2006.01)
*A61N 7/00* (2006.01)
(Continued)

(52) U.S. Cl.
CPC ............... *A61N 7/00* (2013.01); *A61B 5/055* (2013.01); *A61N 7/02* (2013.01); *G06T 7/248* (2017.01);
(Continued)

(58) Field of Classification Search
CPC .. A61B 2017/00084; A61B 2019/5236; A61B 5/015; A61B 5/055;
(Continued)

(56) References Cited

U.S. PATENT DOCUMENTS

2004/0022413 A1* 2/2004 Albus ...................... G06T 7/20
382/103
2004/0076262 A1* 4/2004 Shao ...................... A61B 6/037
378/196

(Continued)

OTHER PUBLICATIONS

Auboiroux, Vincent, et al. "Ultrasonography-based 2D motion-compensated HIFU sonication integrated with reference-free MR temperature monitoring: a feasibility study ex vivo." Physics in medicine and biology 57.10 (2012): N159.*
(Continued)

*Primary Examiner* — Nirav G Patel
(74) *Attorney, Agent, or Firm* — Morgan, Lewis & Bockius LLP

(57) ABSTRACT

During a focused-ultrasound or other non-invasive treatment procedure, the motion of the treatment target or other object(s) of interest can be tracked in real time based on the comparison of treatment images against a reference library of images that have been acquired prior to treatment for the anticipated range of motion and have been processed to identify the location of the target or other object(s) therein.

40 Claims, 5 Drawing Sheets

(51) Int. Cl.
  *A61B 5/055* (2006.01)
  *A61N 7/02* (2006.01)
  *G06T 7/73* (2017.01)
  *G06T 7/246* (2017.01)
  *A61B 5/01* (2006.01)
  *A61B 17/00* (2006.01)
  *A61B 90/00* (2016.01)

(52) U.S. Cl.
  CPC ............... *G06T 7/74* (2017.01); *A61B 5/015* (2013.01); *A61B 2017/00084* (2013.01); *A61B 2090/374* (2016.02); *A61N 2007/0056* (2013.01); *F04C 2270/041* (2013.01); *G06T 2207/10088* (2013.01); *G06T 2207/10132* (2013.01); *G06T 2207/30004* (2013.01); *G06T 2207/30096* (2013.01)

(58) Field of Classification Search
  CPC .... A61N 2007/0056; A61N 7/00; A61N 7/02; G06T 2207/10088; G06T 2207/10132; G06T 2207/30004; G06T 2207/30096; G06T 7/0044; G06T 7/204
  See application file for complete search history.

(56) References Cited

U.S. PATENT DOCUMENTS

| | | | |
|---|---|---|---|
| 2005/0053196 A1 | 3/2005 | Mostafavi | |
| 2005/0215904 A1* | 9/2005 | Sumanaweera | A61B 8/14 600/458 |
| 2010/0067739 A1 | 3/2010 | Mostafavi et al. | |
| 2011/0178444 A1* | 7/2011 | Slayton | A61B 8/48 601/3 |
| 2012/0245453 A1* | 9/2012 | Tryggestad | A61B 6/463 600/413 |
| 2013/0023862 A1* | 1/2013 | Marrouche | A61N 7/02 606/3 |
| 2013/0030283 A1* | 1/2013 | Vortman | A61B 8/4245 600/411 |
| 2014/0073904 A1* | 3/2014 | Biber | A61B 6/527 600/410 |

OTHER PUBLICATIONS

Marquet, F., et al. "Optimal transcostal high-intensity focused ultrasound with combined real-time 3D movement tracking and correction." Physics in medicine and biology 56.22 (2011): 7061.*
International Application No. PCT/IB2013/000321, International Preliminary Report on Patentability dated Aug. 21, 2014, 9 pages.
International Application No. PCT/IB2013/000321, International Search Report and Written Opinion dated Jul. 6, 2013, 13 pages.
de Senneville et al., "Atlas-Based Motion Correction for On-Line MR Temperature Mapping", International Conference on Image Processing, vol. 4, 2004, pp. 2571-2574.
de Senneville et al., "Real-Time Adaptive Methods for Treatment of Mobile Organs by MRI-Controlled High-Intensity Focused Ultrasound", Magnetic Resonance in Medicine, vol. 57, 2007, pp. 319-330.
Neicu et al., "Synchronized Moving Aperture Radiation Therapy (SMART): Average Tumour Trajectory for Lung Patients", Physics in Medicine and Biology, vol. 48, 2003, pp. 587-598.

* cited by examiner

REFERENCE-BASED MOTION TRACKING DURING NON-INVASIVE THERAPY

CROSS-REFERENCE TO RELATED APPLICATION

This application is a U.S. National Phase Application of PCT/IB2013/000321, filed Feb. 6, 2013, which claims priority to and the benefit of, and incorporates by reference herein in their entireties, U.S. Provisional Patent Applications No. 61/595,338 and No. 61/595,341, both filed on Feb. 6, 2012. Reference is also made to the PCT Application of PCT/IB2013/000345, entitled "Reference Library Extension During Imaging of Moving Organs," filed on Feb. 6, 2013.

TECHNICAL FIELD

The present invention relates, in general, to image-guided non-invasive therapy and, in particular, to image-based tracking of moving tissues or organs.

BACKGROUND

Magnetic resonance imaging (MRI) may be used in conjunction with ultrasound focusing, or other non-invasive treatment modalities, in a variety of medical applications. Ultrasound penetrates well through soft tissues and, due to its short wavelengths, can be focused to spots with dimensions of a few millimeters. As a consequence of these properties, ultrasound can be used for non-invasive, highly localized surgery—for example, to ablate or coagulate cancerous tissue without causing significant damage to surrounding healthy tissue. An ultrasound focusing system generally utilizes an acoustic transducer surface, or an array of transducer surfaces, to generate an ultrasound beam. The transducer may be geometrically shaped and positioned such that the ultrasonic energy is focused at a "focal zone" corresponding to the target tissue mass within the patient. During wave propagation through the tissue, a portion of the ultrasound energy is absorbed, leading to increased temperature and, eventually, to cellular necrosis—preferably at the target tissue mass in the focal zone. The individual surfaces, or "elements," of the transducer array are typically individually controllable, i.e., their phases and/or amplitudes can be set independently of one another (e.g., using a "beamformer" with suitable delay and amplifier circuitry for the elements), allowing the beam to be steered in a desired direction and focused at a desired distance and the focal zone properties to be shaped as needed. Thus, the focal zone can be rapidly displaced and/or reshaped by independently adjusting the amplitudes and phases of the electrical signal input into the transducer elements.

In MRI-guided focused-ultrasound (MRgFUS) methods, MRI serves to visualize both the target tissue and the ultrasound focus. Generally, an MRI system 100, as depicted in FIG. 1, includes a static-field magnet 102, one or more gradient-field coils 104, a radio-frequency (RF) transmitter 106, and an RF receiver (not shown). (In some embodiments, the same device is used alternately as RF transmitter or receiver.) The magnet includes a region 108 for receiving a patient 110 therein, and provides a static, relatively homogeneous magnetic field over the patient. Time-variable magnetic field gradients generated by the gradient-field coils 104 are superposed with the static magnetic field. The RF transmitter 106 transmits RF pulse sequences over the patient 110 to cause the patient's tissues to emit a (time-varying) RF response signal, which is integrated over the entire (two- or three-dimensional) imaging region and sampled by the RF receiver to produce a time series of response signals that constitute the raw image data. This raw data is passed on to a computation unit 112. Each data point in the time series can be interpreted as the value of the Fourier transform of the position-dependent local magnetization at a particular point in k-space (i.e., wavevector space), where the wavevector k is a function of the time development of the gradient fields. Thus, by Fourier-transforming the time series of the response signal, the computation unit 112 can reconstruct a real-space image of the tissue (i.e., an image showing the measured magnetization-affecting tissue properties as a function of spatial coordinates) from the raw data. The real-space magnetic-resonance (MR) image may then be displayed to the user. The MRI system 100 may be used to plan a medical procedure, as well as to monitor treatment progress during the procedure. For example, MRI may be used to image an anatomical region, locate the target tissue (e.g., a tumor) within the region, guide the beam generated by the ultrasound transducer 114 to the target tissue, and/or monitor the temperature in and surrounding the target tissue.

Patient motion during treatment, such as periodic motion due to respiration or random movements, can pose a considerable challenge to therapeutic efficacy and safety. Compensation for motion is necessary to ensure that the ultrasound beam remains focused on the target and does not damage the surrounding healthy tissues. In image-guided systems (such as MRgFUS systems), motion compensation is generally accomplished by tracking the target (directly or indirectly) in the images and steering the ultrasound beam based on the tracked position. One approach to target tracking involves determining the coordinates of a set of one or more identifiable features, or "anatomical landmarks," that can be located in each image; and computing the motion of the target, which is presumed to be at a fixed location relative to the landmarks, based on these coordinates. In an alternative approach, the relative shifts between successive images are determined by correlating one image with a large number of computationally shifted copies of the other image, and selecting the shifted image that provides the best match. In either case, significant image-processing time is expended to determine the target location, reducing the effective imaging rate and often impeding real-time motion compensation. In some cases, delays in recognizing and quantifying target motion cause beam-targeting inaccuracies within a tolerable range. Often, however, it becomes necessary to stop the treatment process and correct for any misalignment due to displacement of the target tissue or organ before treatment can be resumed. This results in significant inefficiencies in the treatment process, and may generate significant delays.

Accordingly, there is a need for improved motion-tracking approaches that facilitate tracking the target, and compensating for its motion, in real time during treatment.

SUMMARY

The present invention provides systems and methods for tracking the motion of a treatment target or other objects of interest in real time during an image-guided treatment procedure. Compared with conventional tracking approaches, various embodiments significantly reduce the image-processing time required during treatment by utilizing a library of reference images that are, generally, acquired and processed prior to treatment. The reference images cover an anticipated range of motion (e.g., a complete respiratory cycle) and are processed to (directly or indirectly) locate the object(s) of interest therein; the locational information is stored along with the images. During treatment, the anatomical region of interest may be imaged repeatedly, preferably in real time, and the acquired images may be compared and matched against the images in the reference library based on image similarity. If a sufficiently closely matching reference image is identified, the location of each object of interest in that reference image is deemed to be the location of the respective object in the treatment image as well. Thus, without requiring any further processing, the location of the object(s) of interest in the treatment image can be readily inferred from the locational information stored with the matching reference. Because image matching is, generally, computationally less involved then detecting and localizing objects within an image, this method can achieve significant savings in processing time during treatment, thus facilitating real-time tracking.

Accordingly, in one aspect, the invention provides a method for tracking one or more (generally moving) anatomical objects of interest during a treatment sequence. The anatomical object of interest may be the target of the treatment, e.g., a tumor or tissue region to be treated with focused ultrasound. Alternatively, the object of interest may be an organ or tissue other than the target, such as, e.g., an organ or tissue near the target whose temperature needs to be monitored, or an organ or tissue that ought to be avoided by the ultrasound (or other treatment) beam, either because it is particularly vulnerable to damage from ultrasound or because it would otherwise, due to its material properties (such as ultrasound reflectivity), interfere with the treatment of the target. Often, multiple objects (e.g., a target and one or more tissue regions to be avoided) are tracked simultaneously in order to ensure both treatment efficacy and safety.

The method involves, prior to the treatment sequence, acquiring a series of reference images (i.e., at least one image, and typically a plurality of images) of an anatomical region that includes the anatomical object(s) of interest during motion thereof (each reference image corresponding to a different stage of the motion), and processing the images to determine, for each image, one or more locations therein that are associated with the object(s) of interest. Herein, a "location associated with the object(s) of interest" may be the location of the object of interest itself, or the location of another object—typically an anatomical landmark that is easily discerned in the images (e.g., by virtue of material properties that result in a high contrast to surrounding tissues in the image)—whose position relative to the object of interest is known and, usually, fixed. The images may, e.g., be MR or other tomographic images. Further, unless otherwise apparent from context, the term "images," as used herein, may refer to real-space images (e.g., reconstructed MR images), the raw data from which they are derived, or both.

During the treatment sequence, "treatment images" of the anatomical region are acquired and correlated to the reference images based on similarity, and the object(s) of interest are tracked in the treatment images based on the location(s) associated with the object(s) in the correlated reference images. In some embodiments, image similarity is determined from the raw data. The term "treatment sequence," as used herein, refers to a sequence of one more exposures of an anatomical target to therapeutic energy (e.g., ultrasound). A complete treatment procedure may include a single treatment sequence or a plurality of time-separated treatment sequences. In embodiments where the treatment includes multiple time-separated treatment sequences (each including a single exposure or a sequence of exposures), the treatment images taken in one treatment sequence may be stored and analyzed to serve as reference images in the next treatment sequence.

In some embodiments, processing the reference image includes identifying an anatomical landmark, or multiple anatomical landmarks, in each of the reference images, and tracking the anatomical object during the treatment sequence involves inferring the location of the object in the treatment images from the location of the anatomical landmark in the corresponding reference images. In embodiments where the tracked anatomical object itself is treated, the method may further include steering a therapeutic energy beam, such as a focused ultrasound beam, onto the object based on the tracking. In embodiments where a target other than the tracked anatomical object is treated, the method may include shaping the energy (e.g., ultrasound) beam so as to avoid the anatomical object based on the tracking. In some embodiments, the method further includes monitoring a temperature in the anatomical region by performing baseline subtraction between the treatment images and the corresponding reference images. The method may also include adding a treatment image to the series of reference images. Further, it may include comparing motion of the tracked object against the series of reference images and, based thereon, smoothing the tracked motion and/or detecting a tracking error.

In another aspect, the invention is directed to a system for tracking a moving anatomical object during a treatment sequence. The system includes an imaging apparatus (e.g., an MRI apparatus), operable in conjunction with a treatment apparatus (e.g., an ultrasound transducer), for acquiring a series of reference images of an anatomical region comprising the object prior to the treatment sequence (the series capturing the object during motion thereof and each reference image corresponding to a different stage of the motion) and for acquiring treatment images of the anatomical region during the treatment sequence. Further, the system includes a computation unit configured to process the reference images to determine a location associated with the object for each reference image, correlate the treatment images to corresponding reference images based on similarity therebetween (e.g., using raw image data), and track the object in the treatment images based on the location associated with the object in the corresponding reference images.

The computation unit may be configured to identify, in each of the reference images, at least one anatomical landmark whose location is fixed relative to a location of the object, and to track the target by inferring the location of the target from the location of the anatomical landmark in the corresponding reference image. The computation unit may further be configured to focus a therapeutic energy (e.g., ultrasound beam) generated by the treatment apparatus onto the object based on the tracking, or (if a target other than the tracked anatomical object is being treated) to shape the beam so as to avoid the object based on the tracking. The computation unit may also be configured to monitor a temperature in the anatomical region by performing baseline subtraction between the treatment images and the corresponding reference images. Further, the computation unit may be configured to compare motion of the tracked object against the series of reference images and, based thereon, smooth the tracked motion and/or detect a tracking error.

The computation unit may also add a treatment image to a previously acquired series of reference images. In some embodiments, the treatment sequence is part of a treatment procedure comprising a plurality of time-separated treatment sequences (each comprising at least one exposure of an anatomical target to therapeutic energy), and the computation unit is configured to use a treatment image obtained during a first one of the treatment sequences as a reference image for a subsequent second one of the treatment sequences.

BRIEF DESCRIPTION OF THE DRAWINGS

The foregoing will be more readily understood from the following detailed description of the invention, in particular, when read in conjunction with the drawings, in which.

DETAILED DESCRIPTION

The present invention provides systems and methods for tracking the motion of an object of interest, e.g., a treatment target, in real time during an image-guided procedure. The procedure may, for example, involve the application of focused ultrasound to (i.e., the sonication of) a tissue or organ for the purpose of heating it, either to necrose, ablate, or otherwise destroy the tissue if it is, e.g., cancerous, or for non-destructive treatments such as pain amelioration or the controlled inducement of hyperthermia. Ultrasound may also be used for other, nonthermal types of treatment, such as, e.g., neuromodulation. Alternatively, the procedure may use different forms of therapeutic energy, such as, e.g., radio-frequency (RF) radiation, X-rays or gamma rays, or charged particles, or involve other treatment modalities such as cryoablation. Motion tracking in various treatment procedures may serve to guide the therapeutic energy beam onto the target and/or around other, non-target tissues and organs, i.e., to adjust the beam focus, profile, and/or direction based on images of the affected anatomical region, which may, in some embodiments, also visualize the beam focus. MRI is a widely used technique for such image-based motion tracking. However, other imaging techniques, including, e.g., X-ray imaging, X-ray computed tomography (CT), or ultrasound imaging, may also be used and are within the scope of the present invention. An exemplary system for implementing methods in accordance with various embodiments is an MRgFUS system, such as the one depicted in FIG. 1, with a suitable image-processing and control facility as described in detail below with reference to FIG. 4.

Figure 2:
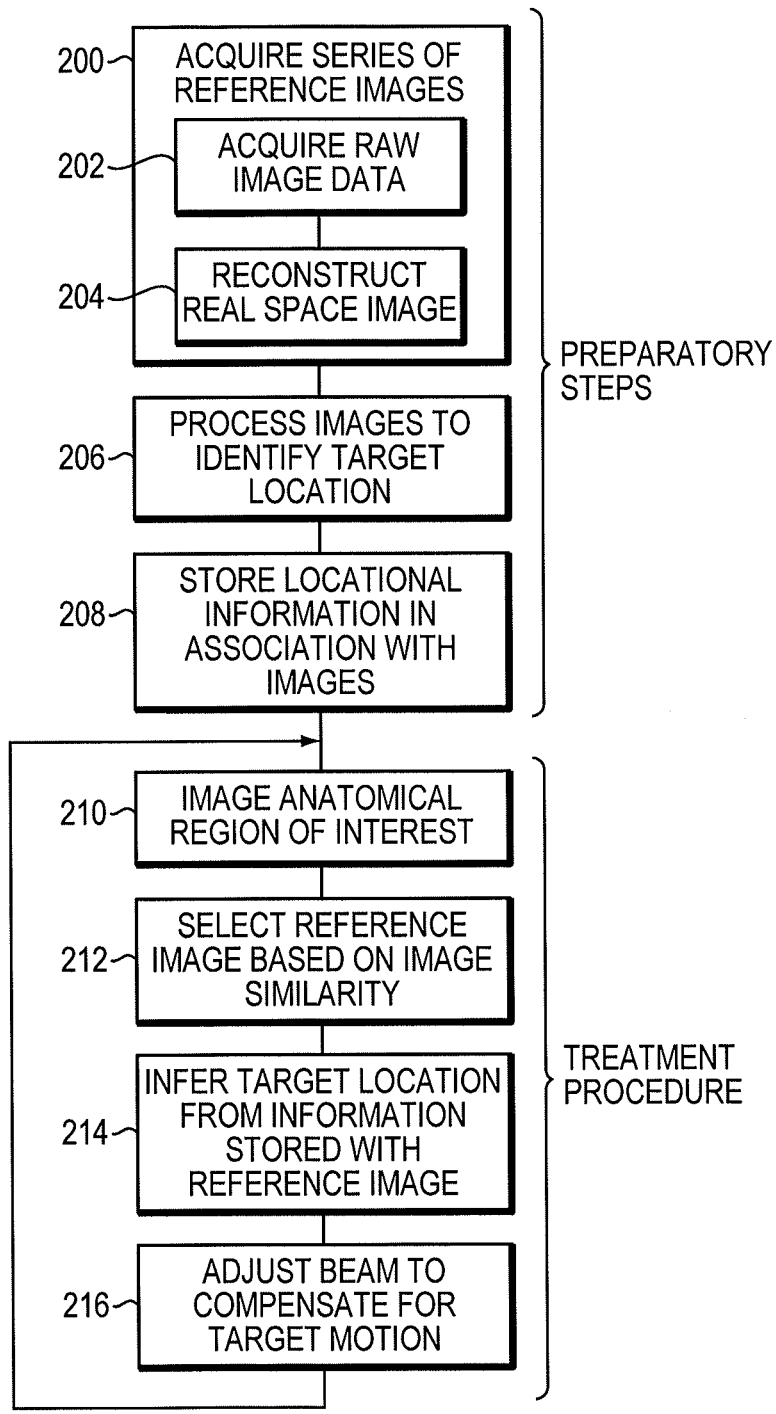
FIG. 2 is a flow chart illustrating a tracking method in accordance with various embodiments.

FIG. 2 illustrates methods for real-time motion tracking in accordance with various embodiments. For ease of reference, the following description only refers to target tracking; it should be understood, however, that the same methods generally apply as well to the tracking of other organs or tissues of interest (such as organs vulnerable to damage from the therapeutic beam). The method includes preparatory steps performed prior to the procedure of interest, as well as steps executed during the procedure. In a first preparatory step 200, a series of images of an anatomical region including the target is acquired during motion thereof. Each image typically corresponds to a different stage of motion, and the series collectively covers the anticipated range of motion. For example, the series of images may be taken in regular intervals during a complete respiratory cycle. As another example, the anatomical region of interest within a patient may be monitored for a certain time period to capture a range of positions resulting from inadvertent sporadic motions. In MRI-based methods, acquiring the images typically involves, first, acquiring raw, k-space MR signals (step 202), and then reconstructing real-space images from the raw data (step 204). Both k-space and real-space image data are complex-valued (i.e., have a magnitude and phase or, expressed differently, real and imaginary parts).

In the next step 206, the real-space images are processed to determine coordinates associated with the target, such as the target coordinates themselves or coordinates of anatomical landmarks located at fixed positions relative to the target. This step may be performed by any of a number of feature-detection or tracking methods known to those of skill in the art. In some embodiments, the target or landmark location is determined for each image separately in absolute coordinates within the image frame (e.g., in terms of row and column numbers) using, e.g., edge detection or blob detection. In other embodiments, relative changes in the target or landmark locations (expressed, e.g., in coordinate differences or translation/motion vectors) between different images are determined. For example, the location of the target in the first image of the series may arbitrarily be designated as the origin, and the location of the target in subsequent images may be measured relative to that origin. Motion vectors can be obtained by pixel-based ("direct") methods such as block-matching algorithms, phase-correlation and frequency-domain methods, pixel recursive algorithms, Bayesian estimators (e.g., a maximum a posteriori probability (MAP) estimate or a Markov random field model), and/or optical flow methods, as well as by feature-based ("indirect") methods that match corresponding features (such as, e.g., Harris corners) between images. Block-matching algorithms, for instance, involve computationally shifting a portion (or "block") of the first image by a large number of known vectors and correlating the resulting copies of the block against the subsequent image to identify the best match. Importantly, the computational cost associated with determining the target location is of reduced importance in selecting an appropriate method because the image-processing step 206 is generally carried out before, not concurrently with, target tracking in real time.

The locational information derived from the images (in step 206) is stored along and in association with respective (k-space and/or real-space) images in a reference library (step 208). For example, each reference image may be combined with its associated locational information into a reference record (which may include one or more data files). Alternatively, the reference images and the locational information may be stored in different data structures and/or at different memory locations, and an additional database may link each image with the associated locational information.

The reference library built in the preparatory steps 200-208 is used subsequently during the procedure of interest for real-time target tracking. This means, in some embodiments, that the preparatory steps are completed before treatment of the target commences. In other embodiments, the preparatory steps for a particular treatment sequence are taken during an earlier treatment sequence. For example, focused-ultrasound ablation of a tumor may be carried out in two or more phases: a first phase during which the central region of the tumor is targeted, and one or more subsequent phases in which the peripheral regions of the tumor are exposed to ultrasound. Since the risk to healthy tissue surrounding the tumor increases as treatment progresses, so may the need for accurate, real-time imaging. Therefore, motion tracking during the first phase may proceed at an imaging rate low enough to permit target localization by conventional means (i.e., means that do not rely on a reference library), and motion tracking during the later phase(s) may utilize the treatment images from the first phase as reference images to enable much higher imaging rates. In general, if treatment involves multiple discrete treatment sequences, the same reference library may be used for all sequences, or the reference library may be re-set for each sequence using images obtained during one or more previous sequence as the new reference images. Further, in some embodiments, only a subset of the acquired reference images (e.g., every other image taken during a respiratory cycle) is processed prior to the treatment sequence of interest and used as an initial reference library for target tracking, and the remaining reference images are processed subsequently, during the treatment sequence of interest, to refine the reference library.

During treatment of the target, the anatomical region is imaged repeatedly (step 210), e.g., in some embodiments, every 100 ms. In order to determine the position of the (generally moving) target within each frame, each image of the sequence (or subset thereof) is compared against the images in the reference library, and the closest match is identified using a suitable metric of image similarity (step 212). The comparison may be based, for example, on real-space or k-space image data, i.e., it may involve, but does not necessarily require, the reconstruction of real-space treatment images from the raw data acquired during treatment. Further, it may suffice to compare portions of the images. Typically, the comparison is performed on a pixel-by-pixel basis, where a "pixel" refers to an element of the image data array, which generally stores amplitude and phase values as a function of real-space coordinates or k-space coordinates, respectively. Suitable similarity metrics include, for example, cross-correlation coefficients, the sum of squared intensity differences, mutual information (as the term is used in probability and information theory), ratio-image uniformity (i.e., the normalized standard deviation of the ratio of corresponding pixel values), the mean squared error, the sum of absolute differences, the sum of squared errors, the sum of absolute transformed differences (which uses a Hadamard or other frequency transform of the differences between corresponding pixels in the two images), or complex cross-correlation (for complex images, such as MRI images), and other techniques familiar, to those of skill in the art, in connection with image registration.

In some embodiments, the similarity between the treatment image and the closest reference image, as measured by the chosen similarity metric, is compared against a (metric-specific) similarity threshold, and only if the level of similarity surpasses that of the threshold (which typically means, for metrics that measure the differences, i.e., the dissimilarity, between images, that the value of the metric falls below the threshold value) is the reference image considered a match for the treatment image. In other embodiments, the reference image most similar to the treatment image is deemed a match regardless of the absolute degree of similarity.

Once a matching reference image has been identified, the location of the target can be readily inferred from the previously determined locational information associated with that reference image (step 214). For example, if the stored locational information includes or consists of the target coordinates themselves, these coordinates are taken to be the coordinates of the target in the current treatment image. Thus, the target can be tracked in real time without the need to identify the target or other landmark in reconstructed treatment images. Further, in some embodiments, treatment-image reconstruction itself is unnecessary if each treatment image is correlated to one of the reference images based on the raw data of both images, or a portion thereof. Based on the tracked target coordinates, the ultrasound (or other therapeutic energy) beam may be steered during the treatment procedure to compensate for any target motion (step 216). Similarly, if non-target organs or tissues are tracked, their coordinates may be used to steer and/or shape the ultrasound (or other energy) beam so as to avoid or minimize their exposure of to the therapeutic energy. Particularly, organs vulnerable to damage from the acoustic beam are often of high interest, and the positions of such organs can be taken into account during beam-forming such that the energy beam is shaped so as to heat the target while avoiding damage to sensitive adjacent organs as they move.

In instances where no reference image matching the current treatment image is found, the target (or other object(s) of interest) may be tracked by other means. For example, the target's motion as tracked in the preceding images may be extrapolated to predict the target's position in the current image frame, or the current position may be determined using a complementary image tracking system, such as a respiratory monitoring belt. Even if the target coordinates cannot be updated in real time and target tracking is, as a consequence, temporarily interrupted, the treatment procedure may, in some embodiments, continue for a brief period (e.g., for one or two image frames), and if matching reference images are identified for subsequently acquired treatment images, delays in the procedure are avoided. However, if it is unsafe to skip an image, or if too many successive procedure images cannot be matched against any of the reference-library images, the procedure is either aborted, or interrupted until the target location has been ascertained (e.g., by conventional, computationally more expensive means) and resumed thereafter.

In some embodiments, the reference library is extended based on images obtained in real time during a procedure. For example, if a newly acquired image reveals the position of the target (or other object of interest) to be outside the region collectively represented in the initial reference library, the newly acquired image may be analyzed to determine the location of the target, and added to the reference library along with the locational information. Optionally, treatment may be paused during the image processing and resumed once the image analysis is complete. In extreme cases, the reference library may even be empty at the beginning of a procedure, and reference images may be added successively as the procedure is carried out. This facilitates a design trade-off between accuracy at the expense of computational overhead (where the library is large, for example, and contains images from previous sessions) or computational efficiency when the reduction in accuracy is clinically acceptable (e.g., where reference images from previous sessions are unlikely to be relevant to a current treatment sequence, in which case the reference library is built up during the current sequence).

In applications where the tracked target motion is periodic (such as during a respiratory cycle), reference images are typically taken sequentially during the cycle of motion, and tracking accuracy during the treatment procedure can, thus, be improved by filtering the tracking results against the reference library. For example, the curve that describes target motion over time during treatment may be compared against and smoothed based on the target motion over time during acquisition of the reference library. Furthermore, target motion as reflected in images of the reference library can serve to detect faulty tracking results, e.g., when, at certain points in time, the tracked target seems to move against the trend of motion during that period in the cycle.

In some embodiments, imaging during a procedure is simultaneously used to quantitatively monitor in vivo temperatures. This is particularly useful in MR-guided thermal therapy (e.g., MRgFUS treatment), where the temperature of a treatment area (e.g., a tumor to be destroyed by heat) should be continuously monitored in order to assess the progress of treatment and correct for local differences in heat conduction and energy absorption to avoid damage to tissues surrounding the treatment area. The monitoring (e.g., measurement and/or mapping) of temperature with MR imaging is generally referred to as MR thermometry or MR thermal imaging.

Among various methods available for MR thermometry, the proton resonance frequency (PRF) shift method is often the method of choice due to its excellent linearity with respect to temperature change, near-independence from tissue type, and temperature map acquisition with high spatial and temporal resolution. The PRF shift method is based on the phenomenon that the MR resonance frequency of protons in water molecules changes linearly with temperature (with a constant of proportionality that, advantageously, is relatively constant between tissue types). Since the frequency change with temperature is small, only $-0.01$ ppm/° C. for bulk water and approximately $-0.0096$ to $-0.013$ ppm/° C. in tissue, the PRF shift is typically detected with a phase-sensitive imaging method in which the imaging is performed twice: first to acquire a baseline PRF phase image prior to a temperature change and then to acquire a second phase image after the temperature change—i.e., a treatment image—thereby capturing a small phase change that is proportional to the change in temperature. A map of temperature changes may then be computed from the (reconstructed, i.e., real-space) images by determining, on a pixel-by-pixel basis, phase differences between the baseline image and the treatment image, and converting the phase differences into temperature differences based on the PRF temperature dependence while taking into account imaging parameters such as the strength of the static magnetic field and echo time (TE) (e.g., of a gradient-recalled echo).

If the temperature distribution in the imaged area at the time of acquisition of the baseline image is known, the temperature-difference map can be added to that baseline temperature in order to obtain the absolute temperature distribution corresponding to the treatment image. In some embodiments, the baseline temperature is simply uniform body temperature throughout the imaging region. More complicated baseline temperature distributions are, in some embodiments, determined prior to treatment by direct temperature-measurements in various locations in combination with interpolation and/or extrapolation based on a mathematical fit (e.g., a smooth, polynomial fit).

Figure 3A:
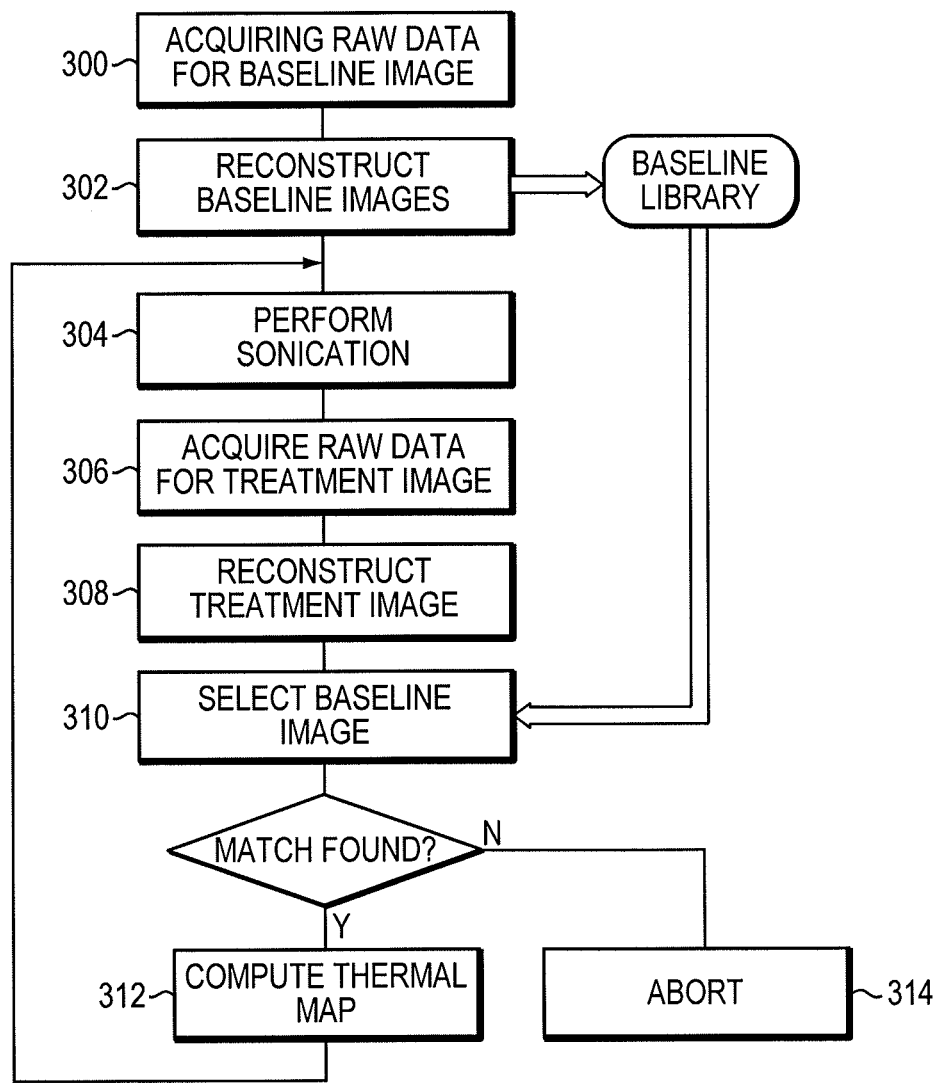
FIG. 3A is a flow chart illustrating a conventional thermometry method.

In the context of MR thermometry, motion tracking can be accomplished by obtaining a library of reference images, as described above, that covers the anticipated range of motion and provides baseline phase maps corresponding to the temperature in the anatomical region prior to treatment. To determine the temperature map for a treatment image, a spatially aligned baseline image is identified (using any of the methods listed above), and the selected baseline and treatment images are then processed to determine the change in temperature. This method is often referred to as multi-baseline thermometry. In its conventional implementation, which is illustrated in FIG. 3A, multibaseline thermometry involves acquiring a library of (real-space) baseline images prior to the sonication or other temperature-affecting treatment (steps 300, 302), performing the sonication (step 304), acquiring raw image data for the treatment region and reconstructing real-space images therefrom (steps 306, 308), selecting a suitable reference image from the baseline library (step 310), e.g., based on an image-similarity criterion, and computing the thermal map from the treatment and reference images (step 312). If no baseline image sufficiently matches the treatment image, e.g., because the target has moved outside the region covered by the images, the process is aborted (step 314). Otherwise, the temperature can continue to be monitored by repeated image acquisition, reference selection, and processing.

Figure 3B:
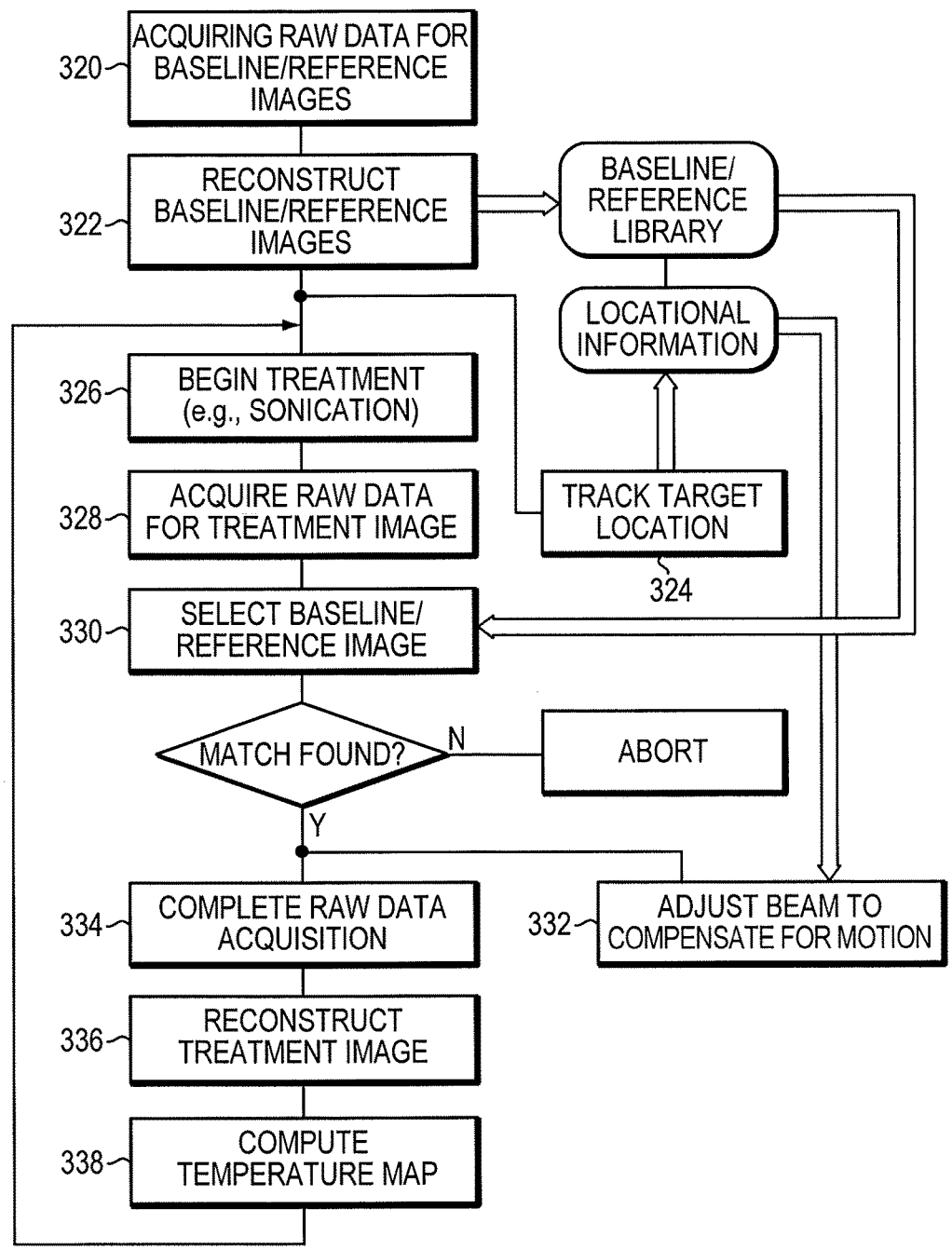
FIG. 3B is a flow chart illustrating a method for thermometry in conjunction with target tracking in accordance with various embodiments.

FIG. 3B illustrates a method that combines motion tracking for the purpose of beam adjustment and thermometry in accordance with an embodiment of the present invention. Again, a library of reference/baseline images that covers the anticipated range of motion is created prior to treatment by acquiring raw image data during different stages of motion (step 320) and reconstructing the real-space reference/baseline images therefrom (step 322). The target (and/or other anatomical object or feature of interest) is tracked in these images (step 324), e.g., relative to a readily identifiable anatomical landmark, by way of image correlation against computationally shifted copies of prior images, or by any of the methods described above with respect to FIG. 2. The identified target location (e.g., row and column numbers within the image or coordinates in some other coordinate system) is stored along or in association with each respective reference image (e.g., in a joint data record, or in a separate database whose entries are linked to the reference images). During the treatment, e.g., after sonication of the target has begun (step 326), image data is acquired for the treatment region (step 328), and a reference/baseline image is selected based on similarity (step 330). As shown, the image data used for comparison with the baseline library need not constitute reconstructed real-space images. Rather, and more typically, raw (k-space) data (of both the treatment image and the baseline images) may be used to identify a suitable reference image. In some embodiments, it is not even necessary to collect a complete k-space image; instead, partial raw data may be used for the purpose of reference selection.

Based on the selected reference image and the target coordinates associated therewith, the sonication or other treatment procedure may be adjusted (step 332), e.g., by beam shaping and/or beam steering, to ensure that the beam focus remains on the target. Further, to facilitate thermometry, the acquisition of raw image data for the treatment region may be completed (step 334) (if has not been already), and the real-space image may be reconstructed (step 336) and further processed in a manner known to those of skill in the art to yield a temperature map (step 338). The imaging and temperature-mapping process may then be repeated for the same or another sub-sonication (i.e., one of a sequence of sonications within the overall sonication procedure). As illustrated, it is possible to reshape or redirect the therapeutic energy beam (step 332) prior to reconstruction of the real-space image (step 336). This way, treatment (e.g., sonication), imaging, and image processing can be performed in parallel, reducing the overall treatment time.

Figure 1:
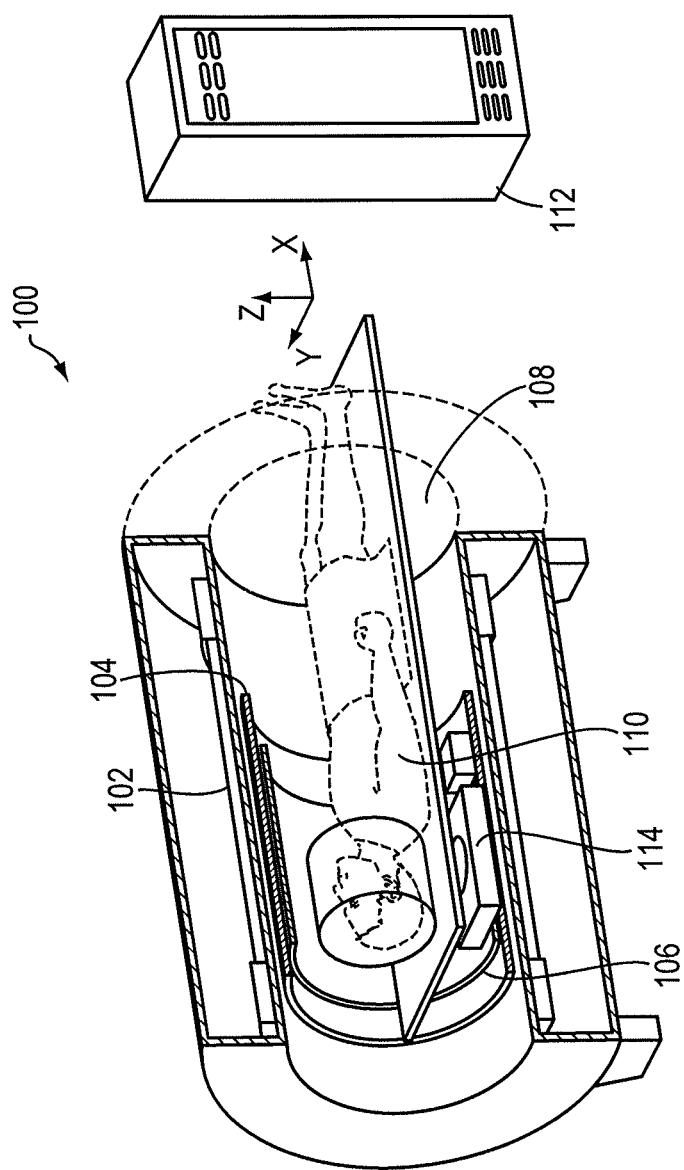
FIG. 1 illustrates an MRI-guided focused ultrasound system in accordance with various embodiments.
Figure 4:
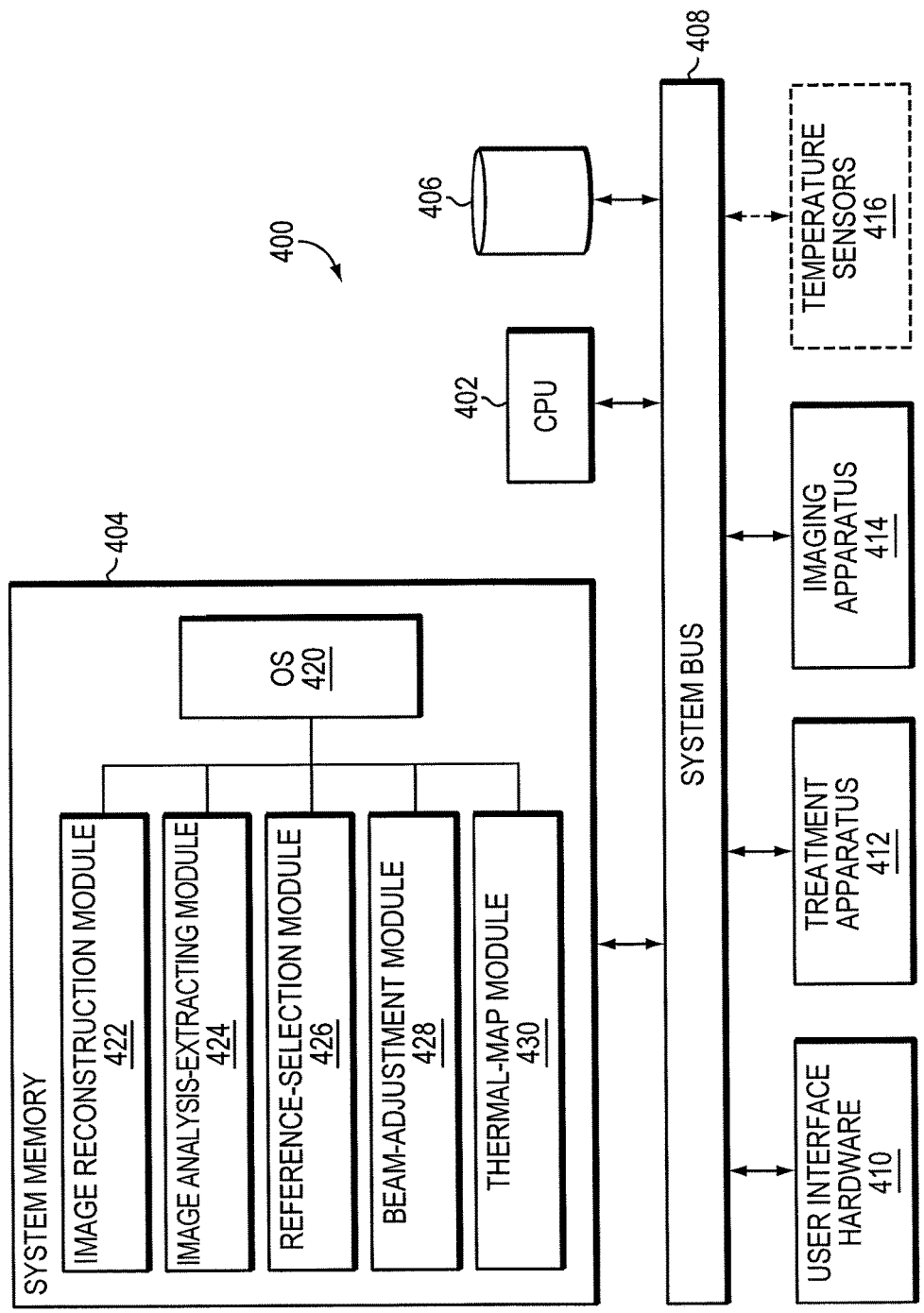
FIG. 4 is a block diagram illustrating an image-processing and control facility in accordance with various embodiments.

Motion-tracking methods in accordance herewith can be implemented using an (otherwise conventional) image-guided treatment system, such as the MRgFUS system 100 depicted in FIG. 1, in conjunction with a suitable image-processing and control facility (e.g., integrated with computation unit 112) in communication with the treatment apparatus (e.g., the beam former setting the phases and amplitudes of an ultrasound transducer array) and the imaging apparatus. The image-processing and control facility may be implemented in any suitable combination of hardware, software, firmware, or hardwiring. FIG. 4 illustrates an exemplary embodiment where the facility is provided by a suitably programmed general-purpose computer 400. The computer includes a central processing unit (CPU) 402, system memory 404, and non-volatile mass storage devices 406 (such as, e.g., one or more hard disks and/or optical storage units). The computer 400 further includes a bidirectional system bus 408 over which the CPU 402, memory 404, and storage devices 406 communicate with each other and with internal or external input/output devices, such as traditional user interface components 410 (including, e.g., a screen, a keyboard, and a mouse) as well as the treatment apparatus 412, the imaging apparatus 414, and (optionally) any temperature sensors 416 facilitating absolute-temperature measurements.

The system memory 404 contains instructions, conceptually illustrated as a group of modules, that control the operation of CPU 402 and its interaction with the other hardware components. An operating system 420 directs the execution of low-level, basic system functions such as memory allocation, file management and operation of mass storage devices 406. At a higher level, one or more service applications provide the computational functionality required for image-processing, motion tracking, and (optionally) thermometry. For example, as illustrated, the system may include an image-reconstruction module 422 for reconstructing real-space images from raw image data received from the imaging apparatus 414, an image analysis module 424 for extracting locational information of the target and/or other object(s) of interest from the reconstructed reference images, a reference-selection module 426 for measuring similarity between treatment and reference images (whether raw or reconstructed images) and selecting suitable reference images based thereon, a beam-adjustment module 428 for computing phase shifts or other parameters of the treatment apparatus to compensate for any detected motion, and a thermal-map module 430 that subtracts reference from treatment images to obtain a temperature difference map and, if the absolute temperature corresponding to the selected reference baseline is known, an absolute-temperature map for the treatment image. The various modules may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages; in some embodiments, different modules are programmed in different languages.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method for tracking a moving anatomical object during a treatment sequence using a treatment device, the method comprising:
   (a) prior to the treatment sequence, (i) using an imaging device to acquire a series of reference images of an anatomical region comprising the anatomical object during motion thereof, each reference image corresponding to a different stage of the motion, and (ii) processing the images to determine, for each image separately, a location associated with the object in absolute coordinates in an imaging coordinate system; and
   (b) during the treatment sequence using the treatment device, (i) acquiring treatment images of the anatomical region using the imaging device, (ii) for a plurality of the treatment images, identifying best-matching reference images corresponding thereto based on a metric of image similarity therebetween, and (iii) tracking the object in the plurality of the treatment images based on the locations associated with the object in the absolute coordinates of the best-matching reference images, wherein the metric of image similarity is determined based on image data corresponding to unreconstructed images.

2. The method of claim 1, wherein the treatment sequence comprises treatment of the anatomical object.

3. The method of claim 2, wherein the treatment sequence comprises steering a focused ultrasound beam onto the object based on the tracking.

4. The method of claim 1, wherein the treatment sequence comprises treatment of a target other than the anatomical object.

5. The method of claim 4, further comprising, during the treatment, shaping a focused ultrasound beam onto the target so as to avoid the anatomical object based on the tracking.

6. The method of claim 1, wherein the treatment sequence is part of a treatment procedure comprising a plurality of time-separated treatment sequences each comprising at least one exposure of an anatomical target to therapeutic energy, wherein at least one of the acquired reference images used during a treatment sequence is a treatment image obtained during a previous treatment sequence.

7. The method of claim 6, wherein each exposure is subjection of the anatomical target to acoustic energy.

8. The method of claim 1, further comprising monitoring a temperature in the anatomical region by performing baseline subtraction between the treatment images and the corresponding reference images.

9. The method of claim 1, wherein processing the reference images comprises identifying at least one anatomical landmark in each of the reference images, the location associated with the object being a location of the at least one anatomical landmark, the location of the at least one anatomical landmark being fixed relative to a location of the object.

10. The method of claim 9, wherein tracking the target comprises inferring the location of the target from the location of the anatomical landmark in the corresponding reference image.

11. The method of claim 1 wherein the location associated with the object is a location of the object.

12. The method of claim 1, wherein images are MRI images.

13. The method of claim 1, wherein the image data corresponding to unreconstructed images comprises raw image data.

14. The method of claim 1, wherein the series comprises at least one image.

15. The method of claim 14, wherein the series comprises a plurality of images.

16. The method of claim 1 further comprising, during the treatment sequence, adding a treatment image to the series of reference images.

17. The method of claim 1 further comprising comparing motion of the tracked object against the series of reference images and, based thereon, detecting a tracking error.

18. The method of claim 1, wherein the anatomical region comprises a second anatomical object and the method further comprises:
processing the acquired series of reference images to determine, for each image, a second location associated with the second object;
correlating at least some of the treatment images to corresponding reference images based on similarity therebetween; and
tracking the second object in the correlated treatment images based on the second location associated with the second object in the corresponding reference images.

19. The method of claim 1, wherein the imaging coordinate system is a coordinate system of an imaging apparatus.

20. The method of claim 1, wherein the imaging coordinate system is a coordinate system of the acquired reference images.

21. The method of claim 1, wherein the metric of similarity comprises at least one of cross-correlation coefficients, a sum of squared intensity differences, mutual information, ratio-image uniformity, a mean squared error, a sum of absolute differences, a sum of squared errors, a sum of absolute transformed differences, or complex cross-correlation.

22. The method of claim 1, wherein the image data corresponding to unreconstructed images comprises k-space image data.

23. A method for tracking a moving anatomical object during a treatment sequence using a treatment device, the method comprising:
(a) prior to the treatment sequence, (i) acquiring a series of reference images of an anatomical region comprising the anatomical object during motion thereof, each reference image corresponding to a different stage of the motion, and (ii) processing the images to determine, for each image, a location associated with the object; and
(b) during the treatment sequence, (i) acquiring treatment images of the anatomical region, (ii) correlating a plurality of the treatment images to corresponding reference images based on similarity therebetween, (iii) tracking the object in the correlated treatment images based on the locations associated with the object in the corresponding reference images, and (iv) comparing motion of the tracked object against motion in the series of reference images and, based thereon, smoothing the tracked motion.

24. A system for tracking a moving anatomical object during a treatment sequence, the system comprising:
(a) an imaging apparatus, operable in conjunction with a treatment apparatus, for (i) acquiring, prior to the treatment sequence, a series of reference images of an anatomical region comprising the object during motion thereof, each reference image corresponding to a different stage of the motion, and (ii) acquiring treatment images of the anatomical region during the treatment sequence; and
(b) a computation unit configured to (i) process the reference images to determine, for each reference image separately, a location associated with the object in absolute coordinates in an imaging coordinate system, (ii) for a plurality of the treatment images, identify best-matching reference images corresponding thereto based on a metric of image similarity therebetween, and (iii) track the object in the plurality of the treatment images based on the location associated with the object in the absolute coordinates of the best-matching reference images, wherein the metric of image similarity is determined based on image data corresponding to unreconstructed images.

25. The system of claim 24, wherein the treatment apparatus comprises an ultrasound transducer.

26. The system of claim 25, wherein the computation unit is further configured to focus an ultrasound beam generated by the transducer onto the object based on the tracking.

27. The system of claim 25, wherein the treatment sequence comprises treatment of a target other than the anatomical object, the computation unit further being configured to shape an ultrasound beam generated by the transducer so as to avoid the object based on the tracking.

28. The system of claim 24, wherein the imaging apparatus comprises an MRI apparatus.

29. The system of claim 24, wherein the treatment sequence is part of a treatment procedure comprising a plurality of time-separated treatment sequences each comprising at least one exposure of an anatomical target to therapeutic energy, the computation unit being configured to use a treatment image obtained during a first one of the treatment sequences as a reference image for a subsequent second one of the treatment sequences.

30. The system of claim 24, wherein the computation unit is further configured to monitor a temperature in the anatomical region by performing baseline subtraction between the treatment images and the corresponding reference images.

31. The system of claim 24, wherein the computation unit is further configured to identify at least one anatomical landmark in each of the reference images, the location associated with the object being a location of the at least one anatomical landmark, the location of the at least one anatomical landmark being fixed relative to a location of the object.

32. The system of claim 31, wherein the computation unit is further configured to track the target by inferring the location of the target from the location of the anatomical landmark in the corresponding reference image.

33. The system of claim 24, wherein the image data corresponding to unreconstructed images comprises raw image data.

34. The system of claim 24, wherein the computation unit is further configured to add a treatment image to the series of reference images.

35. The system of claim 24, wherein the computation unit is further configured to compare motion of the tracked object against the series of reference images and, based thereon, detect a tracking error.

36. The system of claim 24, wherein the anatomical region comprises a second object and the computation unit is further configured to (i) process the reference images to determine, for each reference image, a second location associated with the second object, (ii) correlate at least some of the treatment images to corresponding reference images based on similarity therebetween, and (iii) track the second object in the correlated treatment images based on the second location associated with the second object in the corresponding reference images.

37. The system of claim 24, wherein the imaging coordinate system is a coordinate system of the imaging apparatus.

38. The system of claim 24, wherein the imaging coordinate system is a coordinate system of the acquired reference images.

39. The system of claim 24, wherein the image data corresponding to unreconstructed images comprises k-space image data.

40. A system for tracking a moving anatomical object during a treatment sequence, the system comprising:
  (a) an imaging apparatus, operable in conjunction with a treatment apparatus, for (i) acquiring, prior to the treatment sequence, a series of reference images of an anatomical region comprising the object during motion thereof, each reference image corresponding to a different stage of the motion, and (ii) acquiring treatment images of the anatomical region during the treatment sequence; and
  (b) a computation unit configured to (i) process the reference images to determine, for each reference image, a location associated with the object, (ii) correlate a plurality of the treatment images to corresponding reference images based on similarity therebetween, (iii) track the object in the correlated treatment images based on the location associated with the object in the corresponding reference images, and (iv) compare motion of the tracked object against motion in the series of reference images and, based thereon, smooth the tracked motion.

* * * * *